US009386963B2

(12) United States Patent
Ryan et al.

(10) Patent No.: US 9,386,963 B2
(45) Date of Patent: Jul. 12, 2016

(54) BIOPSY CHANNEL ATTACHMENT ADAPTOR

(71) Applicant: BOSTON SCIENTIFIC SCIMED, INC., Maple Grove, MN (US)

(72) Inventors: Shawn Ryan, Upton, MA (US); Sarah Chamberland, Strubridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

(21) Appl. No.: 14/034,922

(22) Filed: Sep. 24, 2013

(65) Prior Publication Data
US 2014/0088432 A1    Mar. 27, 2014

Related U.S. Application Data

(60) Provisional application No. 61/705,333, filed on Sep. 25, 2012.

(51) Int. Cl.
| A61B 1/00 | (2006.01) |
| A61B 8/00 | (2006.01) |
| A61B 10/04 | (2006.01) |
| A61B 8/12 | (2006.01) |
| A61B 10/02 | (2006.01) |
| A61B 17/00 | (2006.01) |

(52) U.S. Cl.
CPC ............... *A61B 8/4209* (2013.01); *A61B 8/12* (2013.01); *A61B 10/0283* (2013.01); *A61B 10/04* (2013.01); *A61B 2017/00296* (2013.01); *A61B 2017/00486* (2013.01)

(58) Field of Classification Search
USPC .................. 600/104, 114, 136, 154; 606/167.01–167.06
See application file for complete search history.

(56) References Cited

U.S. PATENT DOCUMENTS

| 5,209,219 | A |   | 5/1993 | Hollobaugh |
| 5,336,206 | A | * | 8/1994 | Shichman ..................... 604/534 |
| 5,366,446 | A | * | 11/1994 | Tal ........................ A61B 17/34 604/180 |
| 5,846,183 | A | * | 12/1998 | Chilcoat ....................... 600/136 |
| 6,063,035 | A |   | 5/2000 | Sakamoto et al. |
| 6,113,586 | A | * | 9/2000 | Ouchi ............................. 606/1 |
| 6,293,908 | B1 | * | 9/2001 | Fujikura et al. ............... 600/114 |
| 6,340,352 | B1 | * | 1/2002 | Okada et al. ..................... 601/2 |
| 7,169,167 | B2 | * | 1/2007 | Chu .............................. 606/205 |
| 7,645,231 | B2 |   | 1/2010 | Akiba |
| 7,927,271 | B2 | * | 4/2011 | Dimitriou et al. ............ 600/106 |
| 8,066,630 | B2 | * | 11/2011 | Oberlaender et al. ........ 600/102 |

(Continued)

FOREIGN PATENT DOCUMENTS

| JP | 09-75454 | * | 9/1997 |
| WO | 2011/126812 |  | 10/2011 |

*Primary Examiner* — Matthew J Kasztejna

(74) *Attorney, Agent, or Firm* — Bookoff McAndrews, PLLC

(57) ABSTRACT

An adaptor for an endoscopic device includes (a) a cylindrical core extending from a first end to a second end along a central axis and (b) a collar slidably received over the core. The second end includes first and second slots defining first and second arms which radially expandable toward the axis and away from the axis. The second end is sized and dimensioned to engage an end of a first conduit of a biopsy device. The collar extends from a first end to a second end and being movable from a first position in which the second end of the collar is axially separated from the arms and a second position in which a portion of the collar is positioned over the arms radially compressing the arms to lockingly grasp a free end of a first conduit positioned therebetween to create a fluid-tight seal about the first conduit.

20 Claims, 3 Drawing Sheets

(56) References Cited

U.S. PATENT DOCUMENTS

| | | | |
|---|---|---|---|
| 8,517,918 B2 * | 8/2013 | Smith | 600/114 |
| 2004/0049162 A1 | 3/2004 | Fisher | |
| 2004/0260151 A1 | 12/2004 | Akiba | |
| 2005/0096504 A1 | 5/2005 | Akiba | |
| 2006/0024639 A1 | 2/2006 | Pond | |
| 2009/0088600 A1 * | 4/2009 | Meloul | 600/104 |
| 2010/0022826 A1 * | 1/2010 | Akahoshi et al. | 600/104 |
| 2010/0041949 A1 | 2/2010 | Tolkowsky | |
| 2010/0240956 A1 | 9/2010 | Secrest et al. | |
| 2011/0190662 A1 | 8/2011 | McWeeney | |
| 2012/0010598 A1 | 1/2012 | Frassica et al. | |

\* cited by examiner

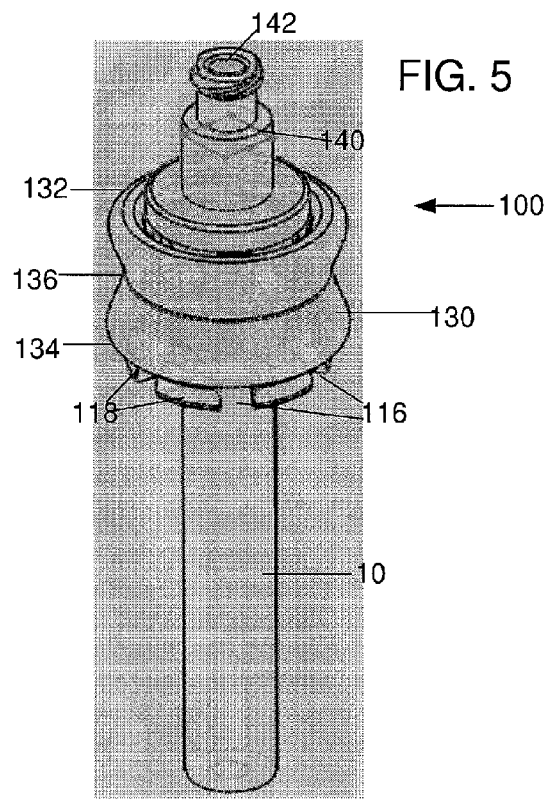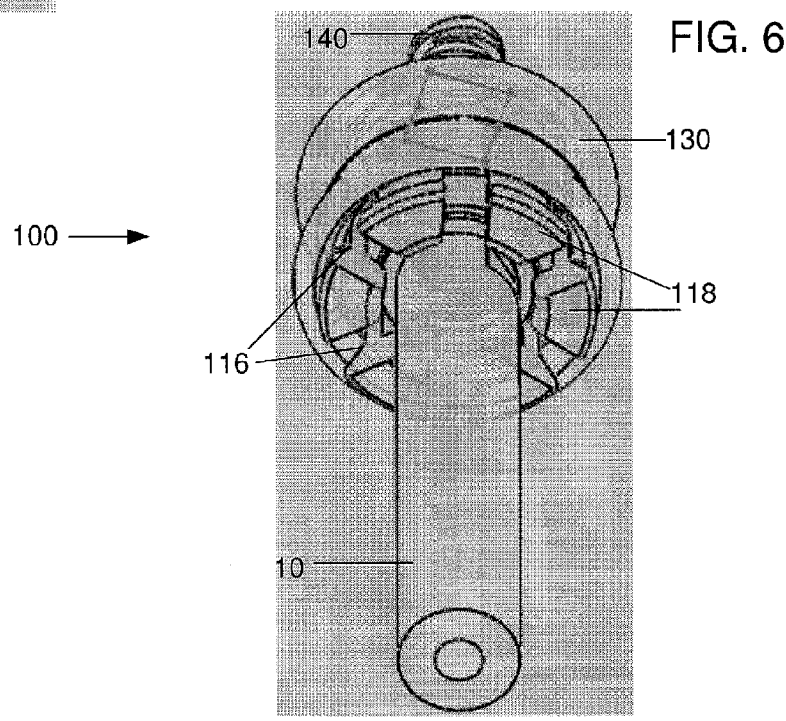

BIOPSY CHANNEL ATTACHMENT ADAPTOR

PRIORITY CLAIM

The present application claims the priority to the U.S. Provisional Application Ser. No. 61/705,333, entitled "Biopsy Channel Attachment Adaptor" filed on Sep. 25, 2012. The specification of the above-identified application is incorporated herewith by reference.

BACKGROUND

Bronchos copy is a technique of visualizing the inside of the airways for diagnostic and therapeutic purposes and includes an insertion of a bronchoscope into a patient's airways through the nose or mouth to allow a physician to examine the airways for abnormalities. An endobronchial ultrasound device may be used to provide further information to aid in diagnosis. Sizes and dimensions of biopsy channels provided in these ultrasound devices vary by manufacturer. Presently, endobronchial ultrasound devices are formed with one of a luer connection and a flange connection to permit engagement thereof with another medical device. A medical device designed for use with a biopsy channel of a particular ultrasound device is not necessarily compatible with a biopsy channel of any other ultrasound device. Thus, the physician is limited to only one particular model of the ultrasound device for use in a treatment procedure. There is a need for an adaptor which can provide a secure, fluid-tight connection between the treatment device and any suitable ultrasound device.

SUMMARY OF THE INVENTION

The present invention relates to an adaptor for an endoscopic device including a cylindrical core extending from a first end to a second end along a central axis, the second end including first and second slots defining first and second arms, the arms being radially expandable toward the central axis and away from the central axis, the second end being sized and dimensioned to engage an end of a first conduit of a biopsy device and a collar slidably received over the core, the collar extending from a first end to a second end and being movable from a first position in which the second end of the collar is axially separated from the arms and a second position in which a portion of the collar is positioned over the arms radially compressing the alms to lockingly grasp a free end of a first conduit positioned therebetween to create a fluid-tight seal about the first conduit.

BRIEF DESCRIPTION OF THE DRAWINGS

Several embodiments of the invention will be described in the following by way of example and with reference to the accompanying drawings in which:

FIG. 5 shows a first partial see-through view of the adaptor of FIG. 1; and

FIG. 6 shows a second partial see-through view of the adaptor of FIG. 1;

DETAILED DESCRIPTION

Figure 1:
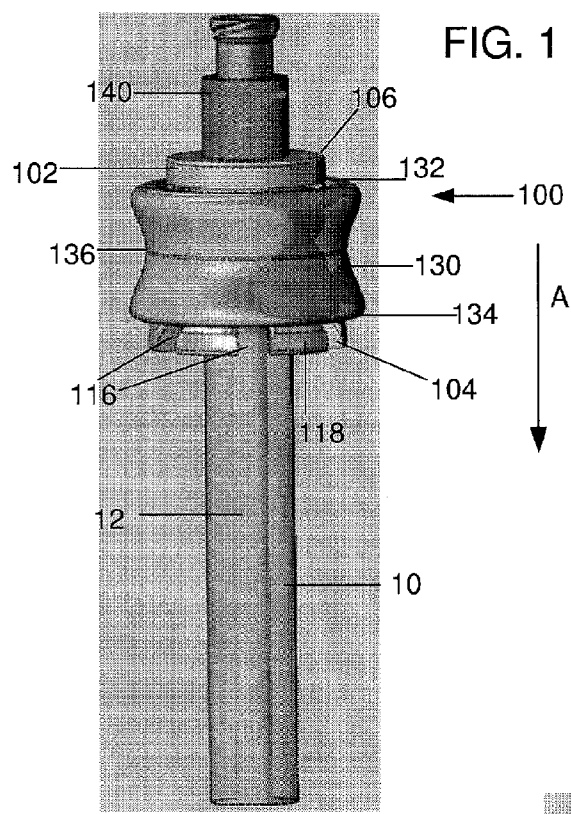
FIG. 1 shows a first perspective view of an adaptor according to an exemplary embodiment of the present invention.

The present invention may be further understood with reference to the following description and the appended drawings, wherein like elements are referred to with the same reference numerals. The present invention relates to endoscopic devices and, more particularly, relates to devices for Endobronchial Ultrasound Aspiration ("EBUS") or for Endobronchial Ultrasound Fine Needle Aspiration ("EBUS FNA"). In particular, the invention relates to an adaptor removably attachable to a distal end of a known biopsy conduit to permit engagement of the biopsy conduit with a conduit of the EBUS device. In an exemplary embodiment, the adaptor according to the invention is removably attached to a distal end of an endobronchial ultrasound endoscopy biopsy conduit to provide a secure, leak-proof connection to the conduit of the EBUS device. The exemplary adaptor according to the invention comprises a substantially cylindrical core with a first end including a plurality of slots distributed about a circumference thereof to define a plurality of arms. This configuration permits the arms to bend radially inward and outward toward and away from, respectively, a central axis of the adaptor. In an exemplary embodiment, the arms are biased toward a radially expanded configuration. A rubber seal fitted within the core includes a conduit extending along the central axis of the adaptor. In an operative configuration, the core with the rubber seal positioned therein is placed over a distal end of the biopsy conduit until the arms are seated over an outer surface thereof. A collar is then slid over the core toward the first end and over at least a portion of the arms to force the arms into a radially compressed configuration over the biopsy conduit forming a fluid-tight seal therewith without damaging the biopsy conduit. A second end of the adaptor opposite the first end includes a luer configured permitting attachment of the conduit of the EBUS device. As will be described in greater detail later on, any of a variety of luer fittings may be used to permit attachment of the biopsy conduit with any known device. Although the exemplary embodiments specifically describe an adaptor interfacing with a biopsy device, it will be understood by those of skill in the art that the adaptor of the present invention may be utilized with any medical device having a first conduit requiring attachment to a second medical device having a second conduit having the same dimensions or different dimensions than the first conduit.

Figure 2:
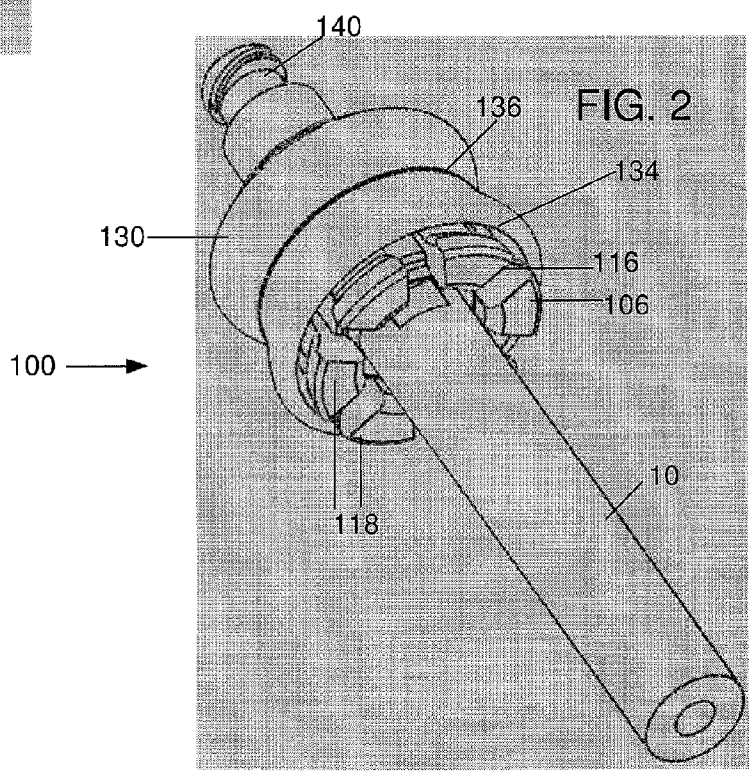
FIG. 2 shows a second perspective view of the adaptor of FIG. 1.
Figure 3:
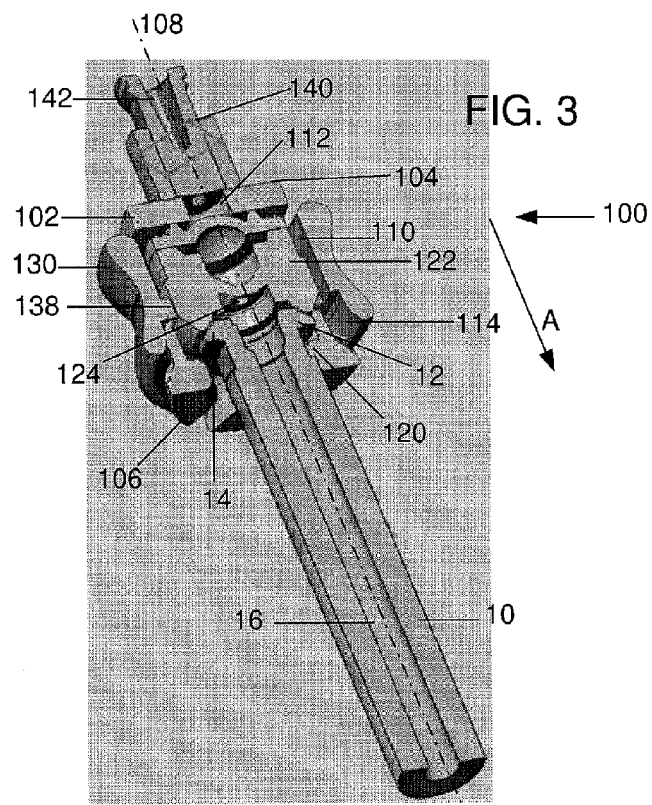
FIG. 3 shows a first cross-sectional view of the adaptor of FIG. 1.
Figure 4:
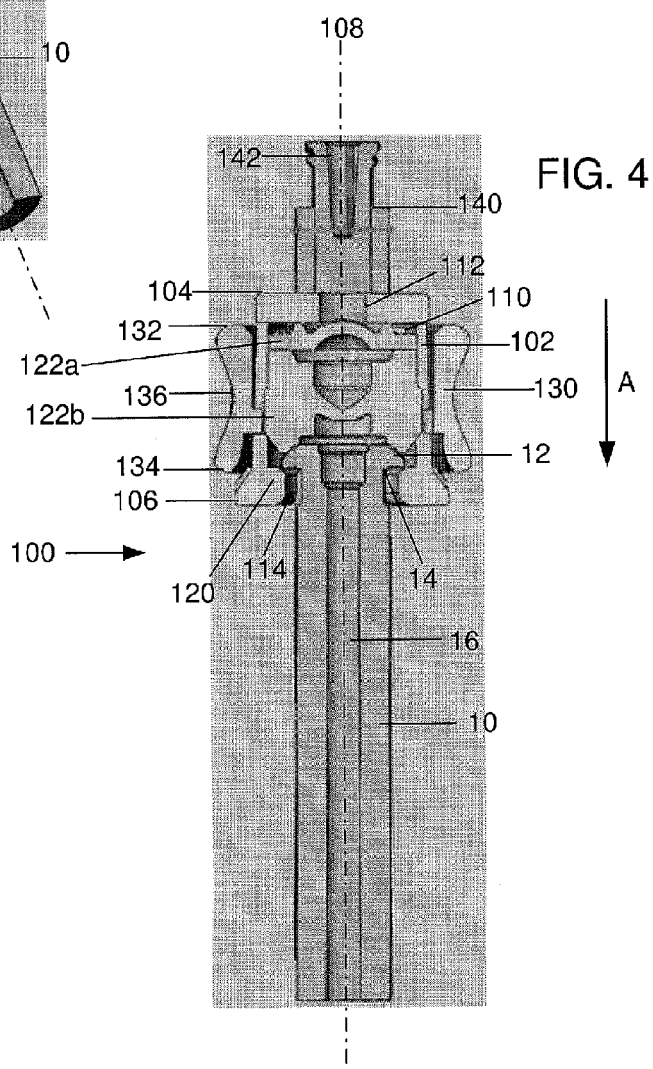
FIG. 4 shows a second cross-sectional view of the adaptor of FIG. 1.

As shown in FIGS. 1-5, an adaptor 100 according to an exemplary embodiment of the present invention comprises a core 102 extending from a first end 104 to a second end 106 along a central longitudinal axis 108. The core 102 may be formed of ABS or a moldable plastic, although other materials may also be used without deviating from the scope of the invention. A channel 110 extends through the core 102 and has first and second openings 112, 114 at the first and second ends 104, 106, respectively. The first opening 112 is dimensioned to permit insertion therethrough of an elongated shaft, for example, a EBUS device (not shown). As will be described in greater detail later on, the EBUS device may be secured to the adaptor via a luer connection as would be understood by those skilled in the art. The second opening 114 is dimensioned to permit slidable insertion of the core 102 over a distal end 12 of a biopsy cannula 10. The second end of the core 102 includes a plurality of slots 116 separating the second end of the core 102 into a plurality of deflectable arms 118. In an exemplary embodiment, the core 102 includes six slots 116 distributed evenly over a circumference of the second end 106 to define six arms 118, although a greater or lesser number of arms 118 may be used to increase or decrease the maximum and minimum diameter of the second opening 114. The arms 118 may be biased toward a radially expanded configuration in which the arms 118 are moved radially outward from the central axis 108. As will be described in greater detail later on, movement of a collar 130 toward the second end 106 over at least a portion of the arms 118 draws the arms to radially inward to reduce a diameter of the opening 114. An inner wall of each of the arms 118 according to this embodiment includes an abutment 120 configured to lockingly engage a flange 14 at the distal end 12 of the cannula 10, as will be described in greater detail later on.

A seal 122 is positioned within the channel 110 with an outer diameter of the seal 122 substantially the same as a diameter of the channel 110 to prevent rotational or axial movement of the seal 122 within the core 102. The seal 122 may be formed of a suitably compressible material such as, for example, rubber or silicone. An opening 124 in the seal 122 is substantially aligned with the central longitudinal axis 108. In an exemplary embodiment, the seal 122 may include first and second components 122a, 122b to aid in manufacturing thereof, as those skilled in the art will understand. In another embodiment, however, the seal 122 may be have a uni-body construction. The seal 122 prevents leakage of fluid flowing to/from the biopsy cannula 10 and a EBUS device (not shown) attached to the adaptor 100. Specifically, as will be described in greater detail with respect to the exemplary method below, the seal 122 directly contacts the biopsy cannula 10 in an operative configuration to seal around the biopsy cannula 10.

The collar 130 which is slidably mounted over an outer surface of the core 102 is substantially cylindrical and extends from a first end 132 to a second end 134. The diameter of the collar 130 at the first and second ends 132, 134 is selected to prevent and/or limit radial compression of the core 102 at these locations. A mid-portion 136 of the core located between the first and second ends 132, 134 has a reduced diameter selected to radially compress the arms 118 when positioned thereover. In an exemplary embodiment, a diameter of the collar 130 is larger at the first and second ends 132, 134, respectively, tapers from the first and second ends 132, 134 toward the reduced diameter of the mid-portion 136. Thus, movement of the collar 130 in the direction A over the arms 118 gradually compresses the arms 118 over the distal end 12 of the cannula 10. In an exemplary embodiment, the collar 130 is formed of a substantially rigid material (e.g., an injection molded plastic, etc.). In an alternate embodiment, the collar 130 may be formed of a substantially flexible material that may be rigid enough to radially compress the arms 118 while being flexible enough to deflect under a counter force applied thereto by the arms 118. Specifically, the collar 130 is able to flex radially outward when a counter-force applied to the collar 130 by the arms 118 exceeds a predetermined threshold. As those skilled in the art will understand, this configuration prevents the arms 118 from permanently damaging the cannula 10 while still maintaining a fluid-tight seal therewith. A diameter of the mid-portion 136 is also selected to prevent the arms 118 from applying excessive force to the cannula 10 (i.e., a compressive force in excess of the capacity of the cannula 10).

An inner wall of the collar 130 according to this embodiment of the invention includes teeth 138 configured to prevent the collar 130 from disengaging the core 102. Specifically, the teeth 138 extend through an elongated slot (not shown) extending through the side wall of the core 102. The slot (not shown) extends parallel to the axis 108 and is closed at the first and second ends 104, 106. The teeth 138 are slidable along the length of the slot (not shown).

The first end 104 of the core 102 includes a luer connection 140 permanently attached thereto with a luer channel 142 open to the channel 110 of the core 102 and to a channel 16 of a cannula 10 attached thereto in an operative configuration. As would be understood by those skilled in the art, the luer connection 140 may be formed in a desired shape and size to permit attachment thereof to a desired device (e.g., the EBUS device). The luer connection 140 may comprise a male luer or female luer connector having any of a barb, threading, locking ring, etc. to conform to the requirements of a particular device to be attached thereto, as those skilled in the art will understand.

In accordance with an exemplary method according to the invention, the collar 130 is initially positioned away from the arms 118 toward the first end 104 of the core 102. In this embodiment, the arms 118 are freed to move under their natural bias to the expanded configuration in which a diameter of the second end 114 of the core 102 is greater than a diameter of the distal end 12 of a cannula 10 to be coupled thereto. The adaptor 100 is then positioned over the distal end 12 until the distal end 12 engages the seal 122 preventing further movement of the adaptor 100 in the direction A. An operator then maintains a force holding the core 102 against the distal end 12 while simultaneously sliding the collar 130 in the direction A until engagement of the teeth 138 with an end of the slot (not shown) prevents further movement thereof. The exemplary adaptor 100 according to the invention permits single-handed use by the operator. Movement of the collar in the direction A causes the collar 130 to apply an increasingly compressive force on the arms 118 moving the arms toward a radially compressed configuration in which they grip the outer surface of the cannula 10. Engagement of the abutments 120 of the arms 118 with the flange 14 of the cannula 10 prevents the cannula 10 from sliding out of engagement with the adaptor 100. A EBUS device (not shown) may then be attached to the luer connection 140 in a desired position and orientation relative to the cannula 10. To remove the adaptor 100 from the cannula 10, the operator moves the collar in a direction opposite the direction A until the radially compressive force on the arms is eliminated and the arms 118 are freed to return to their biased, radially expanded configuration. The cannula 10 may then be safely detached from the adaptor 100.

In an exemplary embodiment the cannula 10 may be a biopsy channel within a working channel of an EBUS device. In a first alternate embodiment of the invention, the adaptor 100 may include a structure (e.g., a hypotube, etc.) insertable into a biopsy port of the endobronchial ultrasound device. The hypotube may have a length and/or diameter selected to permit the hypotube to contact a side wall of the biopsy port if a side load is applied to the biopsy device. Specifically, the hypotube (not shown) may extend from the luer 140 to a position within the biopsy channel 16 by a predetermined distance.

In another alternate embodiment of the invention, the luer 140 may be attached to the adaptor 100 in a manner such that the adaptor 100 acts as a shock absorber if a physician or other user of the endobronchial ultrasound device applies a large side load to the biopsy device. In one embodiment, for example, the core 102 may be formed of a silicone or rubber material to permit deformation thereof under application of a side load thereto. Deflection of the core 102 in this manner prevents the application of the side load onto the luer 140. In another embodiment, the core 102 may include a flexible gasket (not shown) configured to absorb any forces applied thereto, as those skilled in the art will understand.

In yet another alternate embodiment of the invention, the adaptor 100 comprises a mechanical feature (e.g., an abutment, teeth, etc.) on any portion of the adaptor 100 which contacts the cannula 10 in an operative configuration to prevent and/or limit rotation of the cannula 10 relative thereto. In another embodiment, an operator ensures contact between the cannula 10 and the seal 122 frictionally engaging the two to prevent rotation of the cannula 10 relative to the seal 122. In yet another embodiment, rotation may be prevented by using a two-shot molding process with an elastomeric second shot material to add a high friction surface (e.g.,) on the adaptor 100 so that contact between the high friction surface and the cannula 10 prevents rotation thereof.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. An adaptor for an endoscopic device, comprising:
   a cylindrical core extending from a first end to a second end along a central axis, the second end including first and second slots defining first and second arms, the arms being radially moveable toward the central axis and away from the central axis, the second end being sized and dimensioned to engage a free end of a first conduit of a biopsy device;
   a collar slidably received over the core, the collar extending from a first end to a second end and being movable from a first position in which the second end of the collar is axially separated from the arms and a second position in which a portion of the collar is positioned over the arms radially compressing the arms to lockingly grasp the free end of the first conduit positioned therebetween to create a fluid-tight seal about the first conduit, wherein the collar slides from the first end of the core towards the second end of the core when the collar moves from the first position to the second position; and
   a seal positioned within the core and extending from a first end to a second end, the second end of the seal engaging the free end of the first conduit in the second position to form a fluid-tight seal therewith.

2. The adaptor of claim 1, wherein the seal is formed of a rubber material.

3. The adaptor of claim 1, further comprising a luer positioned on the first end of the core, the luer having an opening fluidly connected to the first conduit in the second position.

4. The adaptor of claim 1, wherein a luer is configured and dimensioned to engage a second conduit of a second device to provide a fluid-tight connection between the first and second conduits.

5. The adaptor of claim 4, wherein the second device is an endobronchial ultrasound aspiration device.

6. The adaptor of claim 1, wherein the core is configured to limit axial movement of the collar.

7. The adaptor of claim 1, wherein the arms are biased to a radially expanded configuration.

8. The adaptor of claim 7, wherein a diameter of the collar tapers from the first and second ends to a mid-portion.

9. The adaptor of claim 8, wherein the diameter at the mid-portion is smaller than a diameter of the aims in the radially expanded configuration.

10. The adaptor of claim 1, wherein the first and second arms include radial abutments extending toward the central axis and configured to engage a recess formed over the free end of the first conduit.

11. The adaptor of claim 10, wherein the recess is defined by a flange and extends around the outer circumference of the first conduit.

12. The adaptor of claim 1, wherein the first conduit is a cannula.

13. The adaptor of claim 1, wherein the free end of the first conduit is the proximalmost end of the first conduit.

14. The adaptor of claim 1, wherein the free end of the first conduit tapers.

15. The adaptor of claim 1, wherein the first conduit is removeably engaged with the core.

16. The adaptor of claim 1, wherein the seal surrounds an outer surface of the first conduit.

17. An adaptor for an endoscopic device, comprising:
   a cylindrical core extending from a first end to a second end along a central axis, the second end including first and second slots defining first and second arms, the arms being radially moveable toward the central axis and away from the central axis, the second end being sized and dimensioned to engage an end of a cannula of a biopsy device; and
   a collar slidably received over the core, the collar extending from a first end to a second end and being movable from a first position in which the second end of the collar is axially separated from the arms and a second position in which a portion of the collar is positioned over the arms radially compressing the arms to lockingly grasp the end of the cannula positioned therebetween to create a fluid-tight seal about the cannula, wherein the collar slides from the first end of the core towards the second end of the core when the collar moves from the first position to the second position.

18. The adaptor of claim 17, wherein the core surrounds the cannula.

19. An adaptor for an endoscopic device, comprising:
   a cylindrical core extending from a first end to a second end along a central axis, the second end including first and second slots defining first and second arms, the arms being radially moveable toward the central axis and away from the central axis, the second end being sized and dimensioned to engage a proximalmost end of a first conduit of a biopsy device; and
   a collar slidably received over the core, the collar extending from a first end to a second end and being movable from a first position in which the second end of the collar is axially separated from the arms and a second position in which a portion of the collar is positioned over the arms radially compressing the arms to lockingly grasp the proximalmost end of the first conduit positioned therebetween to create a fluid-tight seal about the first conduit, wherein the collar slides from the first end of the core towards the second end of the core when the collar moves from the first position to the second position.

20. The adaptor of claim 19, wherein the first conduit is removeably engaged with the core.

* * * * *